(12) United States Patent
Lostetter

(10) Patent No.: US 11,351,025 B2
(45) Date of Patent: Jun. 7, 2022

(54) VASCULAR PROSTHESIS WITH FENESTRATION RING AND METHODS OF USE

(71) Applicant: Bolton Medical, Inc., Sunrise, FL (US)

(72) Inventor: Timothy Lostetter, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 0 days.

(21) Appl. No.: 16/433,654

(22) Filed: Jun. 6, 2019

(65) Prior Publication Data

US 2019/0282355 A1    Sep. 19, 2019

Related U.S. Application Data

(63) Continuation of application No. PCT/US2018/019351, filed on Feb. 23, 2018.

(60) Provisional application No. 62/463,071, filed on Feb. 24, 2017.

(51) Int. Cl.
*A61F 2/07* (2013.01)
*A61F 2/06* (2013.01)
*A61F 2/856* (2013.01)
*A61F 2/89* (2013.01)

(52) U.S. Cl.
CPC .................. *A61F 2/06* (2013.01); *A61F 2/07* (2013.01); *A61F 2/856* (2013.01); *A61F 2/89* (2013.01); *A61F 2002/061* (2013.01); *A61F 2002/067* (2013.01); *A61F 2210/0014* (2013.01); *A61F 2250/001* (2013.01)

(58) Field of Classification Search
CPC ........ A61F 2/06; A61F 2002/061; A61F 2/07; A61F 2002/821
See application file for complete search history.

(56) References Cited

U.S. PATENT DOCUMENTS

| | | |
|---|---|---|
| 5,123,917 A | 6/1992 | Lee |
| 5,507,769 A | 4/1996 | Marin et al. |
| 5,755,769 A | 5/1998 | Richard et al. |

(Continued)

FOREIGN PATENT DOCUMENTS

| | | |
|---|---|---|
| CN | 104114201 A | 10/2014 |
| CN | 106344208 A | 1/2017 |

(Continued)

OTHER PUBLICATIONS

International Preliminary Report on Patentability for International Application No. PCT/US2018/019351 dated Aug. 27, 2019.

(Continued)

*Primary Examiner* — Suba Ganesan
(74) *Attorney, Agent, or Firm* — Foley Hoag LLP

(57) ABSTRACT

The vascular prosthesis includes a luminal graft component having at least one fenestration. At least one fenestration ring borders the at least one fenestration and is fixed to the luminal graft component. The fenestration ring includes a main component with two opposing ends and a connecting component. The diameter of the fenestration ring can expand upon insertion of a branch prosthesis through the fenestration ring during implantation at a surgical site. The vascular prosthesis can be implanted in a patient to thereby treat, for example, an arterial aneurysm, spanning a region of an aneurysm that includes at least one arterial branch.

25 Claims, 17 Drawing Sheets

(56) References Cited

U.S. PATENT DOCUMENTS

| | | |
|---|---|---|
| 6,113,623 A | 9/2000 | Sgro |
| 6,171,334 B1 | 1/2001 | Cox |
| 6,280,464 B1 | 8/2001 | Hayashi |
| 6,395,018 B1 | 5/2002 | Castaneda |
| 7,435,253 B1 | 10/2008 | Hartley et al. |
| 7,637,940 B2 | 12/2009 | Kocur et al. |
| 7,763,063 B2 | 7/2010 | Arbefeuille et al. |
| 8,007,605 B2 | 8/2011 | Arbefeuille et al. |
| 8,062,345 B2 | 11/2011 | Ouellette et al. |
| 8,172,895 B2 | 5/2012 | Anderson et al. |
| 8,236,040 B2 | 8/2012 | Mayberry et al. |
| 8,333,800 B2 | 12/2012 | Bruszewski et al. |
| 8,480,725 B2 | 7/2013 | Rasmussen et al. |
| 8,486,129 B2 | 7/2013 | Lautherjung |
| 8,500,792 B2 | 8/2013 | Berra |
| 8,641,752 B1 | 2/2014 | Holm et al. |
| 8,808,351 B2 | 8/2014 | Osborne |
| 8,915,955 B2 | 12/2014 | West et al. |
| 8,926,693 B2 | 1/2015 | Duffy et al. |
| 9,101,455 B2 | 8/2015 | Roeder et al. |
| 9,101,506 B2 | 8/2015 | Arbefeuille et al. |
| 9,259,336 B2 | 2/2016 | Schaeffer et al. |
| 9,364,314 B2 | 6/2016 | Berra et al. |
| 9,375,308 B2 | 6/2016 | Norris |
| 9,439,751 B2 | 9/2016 | White et al. |
| 9,592,112 B2 | 3/2017 | Arbefeuille et al. |
| 9,827,123 B2 | 11/2017 | Arbefeuille et al. |
| 9,861,503 B2 | 1/2018 | Barthold et al. |
| 9,877,857 B2 | 1/2018 | Arbefeuille et al. |
| 10,005,269 B2 | 6/2018 | Hall et al. |
| 10,080,674 B2 | 9/2018 | Yuan et al. |
| 10,299,951 B2 | 5/2019 | Arbefeuille et al. |
| 10,390,930 B2 | 8/2019 | Arbefeuille et al. |
| 10,478,320 B2 | 11/2019 | Shahriari |
| 10,485,684 B2 | 11/2019 | Marmur et al. |
| 10,617,542 B2 | 4/2020 | Chakfe et al. |
| 10,702,406 B2 | 7/2020 | Swift et al. |
| 10,898,357 B2 | 1/2021 | Arbefeuille et al. |
| 10,987,235 B2 | 4/2021 | Eubanks et al. |
| 11,000,359 B2 | 5/2021 | Torrance et al. |
| 2002/0062133 A1 | 5/2002 | Gilson et al. |
| 2002/0188344 A1 | 12/2002 | Bolea et al. |
| 2002/0193872 A1 | 12/2002 | Trout et al. |
| 2004/0059406 A1 | 3/2004 | Cully et al. |
| 2004/0073289 A1 | 4/2004 | Hartley |
| 2005/0102021 A1* | 5/2005 | Osborne ............... A61F 2/07 623/1.13 |
| 2005/0131518 A1* | 6/2005 | Hartley ............... A61F 2/856 623/1.13 |
| 2005/0131519 A1* | 6/2005 | Hartley ............... A61F 2/07 623/1.13 |
| 2005/0131523 A1 | 6/2005 | Bashiri et al. |
| 2006/0015171 A1 | 1/2006 | Armstrong |
| 2006/0020319 A1 | 1/2006 | Kim et al. |
| 2006/0155359 A1 | 7/2006 | Watson |
| 2006/0184226 A1 | 8/2006 | Austin |
| 2007/0055360 A1 | 3/2007 | Hanson et al. |
| 2007/0135904 A1 | 6/2007 | Eidenschink et al. |
| 2007/0244547 A1 | 10/2007 | Greenan |
| 2008/0091260 A1 | 4/2008 | Pomeranz et al. |
| 2008/0132988 A1 | 6/2008 | Jordan |
| 2008/0269867 A1 | 10/2008 | Johnson |
| 2009/0043377 A1 | 2/2009 | Greenberg et al. |
| 2009/0248135 A1 | 10/2009 | Bruszewski et al. |
| 2010/0004730 A1 | 1/2010 | Benjamin et al. |
| 2010/0114290 A1 | 5/2010 | Rasmussen et al. |
| 2010/0121429 A1 | 5/2010 | Greenan et al. |
| 2010/0234932 A1 | 9/2010 | Arbefeuille et al. |
| 2010/0239932 A1 | 9/2010 | Darling et al. |
| 2010/0316830 A1* | 12/2010 | Hartley ............... A61F 2/07 428/64.1 |
| 2011/0100669 A1 | 5/2011 | Lee et al. |
| 2011/0190862 A1 | 8/2011 | Bashir et al. |
| 2011/0257720 A1 | 10/2011 | Peterson et al. |
| 2012/0035714 A1 | 2/2012 | Ducke et al. |
| 2012/0221096 A1 | 8/2012 | Roeder et al. |
| 2012/0271401 A1 | 10/2012 | Bruszewski et al. |
| 2013/0116773 A1 | 5/2013 | Roeder et al. |
| 2013/0116775 A1 | 5/2013 | Roeder et al. |
| 2013/0123900 A1 | 5/2013 | Eblacas et al. |
| 2013/0158648 A1 | 6/2013 | Hartley et al. |
| 2013/0184806 A1 | 7/2013 | Arbefeuille et al. |
| 2013/0282102 A1 | 10/2013 | Peterson |
| 2014/0039597 A9 | 2/2014 | Arbefeuille et al. |
| 2014/0046428 A1 | 2/2014 | Cragg et al. |
| 2015/0105819 A1 | 4/2015 | Becking et al. |
| 2015/0105849 A1 | 4/2015 | Cohen et al. |
| 2015/0202065 A1 | 7/2015 | Shalev et al. |
| 2015/0202067 A1 | 7/2015 | Barrand et al. |
| 2015/0272755 A1 | 10/2015 | Arbefeuille et al. |
| 2015/0335452 A1 | 11/2015 | Rao et al. |
| 2016/0184078 A1 | 6/2016 | Choubey et al. |
| 2016/0296353 A1 | 10/2016 | Skender |
| 2016/0302950 A1 | 10/2016 | Marmur et al. |
| 2017/0135807 A1 | 5/2017 | Arbefeuille et al. |
| 2017/0281382 A1 | 10/2017 | Lostetter et al. |
| 2018/0071123 A1 | 3/2018 | Arbefeuille et al. |
| 2018/0296374 A1 | 10/2018 | Chakfe et al. |
| 2019/0231571 A1 | 8/2019 | Lostetter |
| 2019/0247178 A1 | 8/2019 | Arbefeuille |
| 2019/0247179 A1 | 8/2019 | Lostetter |
| 2019/0247213 A1 | 8/2019 | Lostetter |
| 2019/0269497 A1 | 9/2019 | Arbefeuille |
| 2019/0269498 A1 | 9/2019 | Arbefeuille et al. |
| 2019/0282355 A1 | 9/2019 | Lostetter |
| 2019/0350694 A1 | 11/2019 | Arbefeuille et al. |
| 2020/0352700 A1 | 11/2020 | Torrance et al. |
| 2021/0100669 A1 | 4/2021 | Arbefeuille et al. |

FOREIGN PATENT DOCUMENTS

| | | |
|---|---|---|
| EP | 1847234 A1 | 10/2007 |
| EP | 1847236 A2 | 10/2007 |
| EP | 2471498 A1 | 7/2012 |
| EP | 2517672 A1 | 10/2012 |
| EP | 2735283 A1 | 5/2014 |
| EP | 2740440 A2 | 6/2014 |
| EP | 2745812 A1 | 6/2014 |
| EP | 2745813 A1 | 6/2014 |
| EP | 2749250 A1 | 7/2014 |
| EP | 2749251 A1 | 7/2014 |
| EP | 2606851 B1 | 11/2015 |
| EP | 3040054 A1 | 7/2016 |
| EP | 3068339 A1 | 9/2016 |
| EP | 3078349 A1 | 10/2016 |
| EP | 3272319 A1 | 1/2018 |
| WO | WO-97/03624 A1 | 2/1997 |
| WO | WO-99/29262 A1 | 6/1999 |
| WO | WO-01/60285 A1 | 8/2001 |
| WO | WO-02/083038 A2 | 10/2002 |
| WO | WO-03/099108 A2 | 12/2003 |
| WO | WO-2005/034809 A1 | 4/2005 |
| WO | WO-2005/034810 A1 | 4/2005 |
| WO | WO-2006/037086 A1 | 4/2006 |
| WO | WO-2009/009376 A2 | 1/2009 |
| WO | WO-2009/148594 A1 | 12/2009 |
| WO | WO-2010/024880 A1 | 3/2010 |
| WO | WO-2010/030370 A1 | 3/2010 |
| WO | WO-2010/127040 A1 | 11/2010 |
| WO | WO-2012/116368 A2 | 8/2012 |
| WO | WO-2012/145823 A1 | 11/2012 |
| WO | WO-2015/070792 A1 | 5/2015 |
| WO | WO-2017/218474 A1 | 12/2017 |
| WO | WO-2018/026768 A1 | 2/2018 |

OTHER PUBLICATIONS

International Search Report and Written Opinion for International Application No. PCT/US2018/019351 dated May 7, 2018.

(56) References Cited

OTHER PUBLICATIONS

Extended European Search Report for EP Application No. 21153107.4 dated May 18, 2021.

* cited by examiner

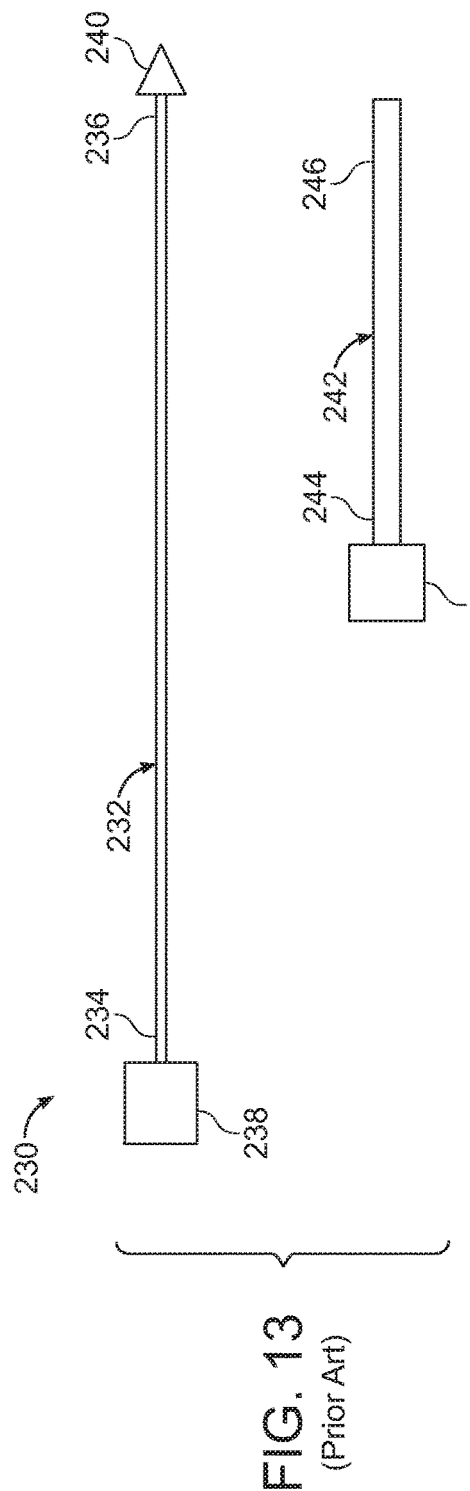
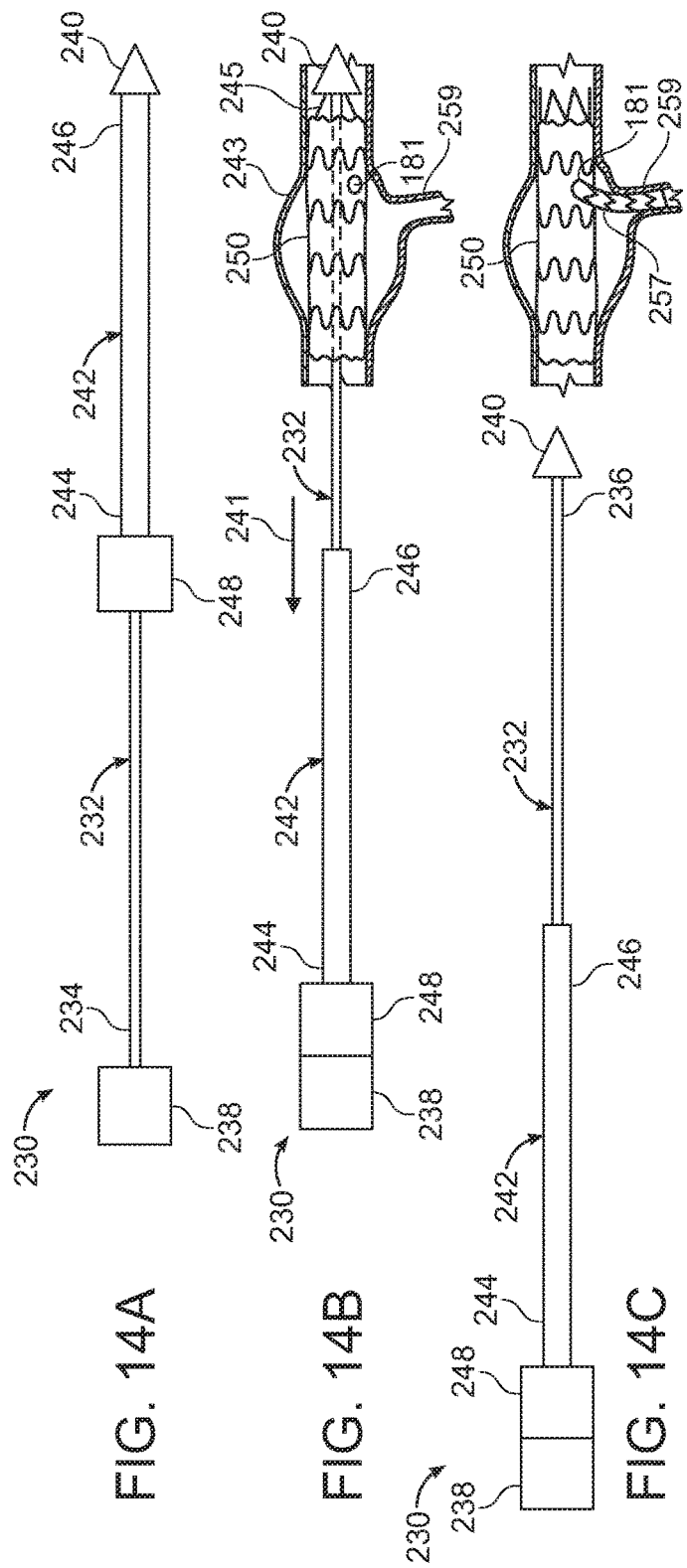

VASCULAR PROSTHESIS WITH FENESTRATION RING AND METHODS OF USE

RELATED APPLICATION

This application is a continuation of International Application No. PCT/US2018/019351, which designated the United States and was filed on Feb. 23, 2018, published in English, which claims the benefit of U.S. Provisional Application No. 62/463,071, filed on Feb. 24, 2017. The entire teachings of the above applications are incorporated herein by reference.

BACKGROUND

Fenestrated endovascular aortic repair (FEVAR) is a minimally invasive procedure to treat aortic aneurysms that span blood vessels arising from the aorta that supply blood to vital organs including the kidneys, intestine and liver. Endovascular grafts employed in FEVAR define fenestrations for insertion of branch prostheses that serve as passageways for blood flow through arterial branches to vital organs following implantation of the endovascular graft. Maximizing blood flow to vital organs and minimizing endoleaks following repair of aneurysms with fenestrated vascular prostheses, such as juxtarenal aortic aneurysms and short-neck abdominal aortic aneurysms, present medical challenges that must be overcome or minimized if additional surgical intervention is to be avoided.

Therefore, a need exits for new and improved endovascular repair devices and methods to treat aortic pathologies, such as juxtarenal and short-neck abdominal aortic aneurysms.

SUMMARY

The present invention relates to vascular prostheses for use in treating and repairing aortic vascular damage, such as vascular damage associated with aortic aneurysms in regions of the aorta having arterial branches that supply blood to vital organs and tissues, including juxtarenal aortic aneurysms and short-neck abdominal aortic aneurysms.

In one embodiment, the invention is a vascular prosthesis that includes a luminal graft component and at least one fenestration ring encompassing at least one fenestration in the luminal graft component. The luminal graft component includes a proximal open end, a distal open end and defines a main lumen extending from the proximal open-end to the distal open end, the luminal graft component defining at least one fenestration. The fenestration ring is fixed to the luminal graft component and defines a variable fenestration ring diameter. The fenestration ring includes a main component having two opposing ends, and a connecting ring component that bridges the two opposing ends to thereby complete configuration of the main component as a ring. The fenestration ring diameter can expand upon insertion of a branch prosthesis through the at least one fenestration ring during implantation of the branch prosthesis.

In another embodiment, the invention is a method for treating an aortic aneurysm, comprising the steps of delivering a vascular prosthesis through an aorta to an aneurysm site of a patient, the aneurysm spanning a region of the aorta that includes at least one arterial branch, the vascular prosthesis being radially and releasably constricted by a vascular prosthesis delivery device, the vascular prosthesis including a luminal graft component having a proximal open end, a distal open end, and defining a main lumen extending from the proximal open end to the distal open end, the luminal graft component defining at least one fenestration encompassed by a fenestration ring that is fixed to the luminal graft component. The fenestration ring defines a variable fenestration ring diameter and includes a main component having two opposing ends, and a connecting component that bridges the two opposing ends to thereby complete configuration of the main components as a ring. The fenestration ring diameter can expand upon insertion of a branch prosthesis through the at least one fenestration ring during implantation the branch prosthesis. The at least one fenestration is aligned with the at least one arterial branch at the aneurysm site of a patient, and the vascular prosthesis is then least partially released from the vascular prosthesis delivery device. At least one branch prosthesis is delivered through the proximal open end or the distal open end of the luminal graft component of the vascular prosthesis, and through the fenestration associated with the respective arterial branch, the branch prosthesis being radially and releasably constricted by a branch prosthesis delivery device. The branch prosthesis delivery device is then released from the vascular prosthesis delivery device, and expansion of the branch prosthesis causes contact at the luminal graft component that increases the variable fenestration ring diameter, thereby forming a seal between the vascular prosthesis and the branch prosthesis, and treating the aortic aneurysm.

The vascular prostheses and methods of the invention have several advantages by, for example, providing the surgeon with increased flexibility to accommodate anatomical variations in the size of arterial branches at an aneurysm. Specifically, the size of a fenestration of a luminal graft component of a vascular prosthesis can be adjusted to better fit a branch prosthesis during implantation by employing the vascular prosthesis and method of the invention. The vascular prostheses of the invention have the additional advantage of improving a seal between the fenestration of the vascular prosthesis of the invention and a branch prosthesis following insertion of the branch prosthesis into the fenestration, and by better securing the branch prostheses, thereby significantly reducing the incidence and severity of endoleaks and resulting complications.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 13 is an exploded side view of one embodiment of a prior art delivery device suitable for use with the invention.

FIG. 14A is a side view of the delivery device shown in FIG. 13 and containing a vascular prosthesis of the invention (not shown) loaded within the introducer sheath of the delivery device.

FIG. 14B is a side view of the delivery device shown in FIG. 14A after retraction of an introducer sheath of the delivery device to expose a vascular prosthesis of the invention or a branch prosthesis during delivery to an aneurysm.

FIG. 14C is a side view of the delivery device shown in FIGS. 14A and 14B after retraction of the delivery device from the vascular prosthesis of the invention or the branch prosthesis, thereby completing implantation of the prosthesis and treatment of an aneurysm in a patient.

DETAILED DESCRIPTION

The features and other details of the invention, either as steps of the invention or as combinations of parts of the invention will now be more particularly described and pointed out in the claims. It will be understood that the particular embodiments of the invention are shown by way of illustration and not as limitations of the invention. The principle features of this invention can be employed in various embodiments without departing from the scope of the invention. It will also be understood that the same number appearing in different drawings represents the same item.

The invention is generally directed to vascular prostheses for use in treating and repairing aortic vascular damage, such as vascular damage associated with an aortic aneurysm in regions of the aorta having arterial branches that supply blood to vital organs and tissues, including juxtarenal aortic aneurysms and short-neck abdominal aortic aneurysms.

A description of example embodiments of the invention follows:

When reference is made herein to a prosthesis, also referred to herein as "stent graft," "stent graft prosthesis," or "vascular prosthesis," to be delivered, or implanted in a patient, the word "proximal" means that portion of the prosthesis or component of the prosthesis that is relatively close to the heart of the patient and "distal" means that portion of the prosthesis or component of the prosthesis that is relatively far from the heart of the patient.

When, however, reference is made to a delivery system or a component of a delivery system employed to deliver, or implant, a prosthesis, the word, "proximal," as employed herein, means closer to the clinician using the delivery system. When reference is made to a delivery system or a component of a delivery system, "distal," as that term is employed herein, means, further away from the clinician using the delivery system.

For clarity, the word "proximate" means "close to," as opposed to the meanings ascribed to "proximal" or "distal" described above with respect to either the prosthesis or a delivery system.

Figure 1:
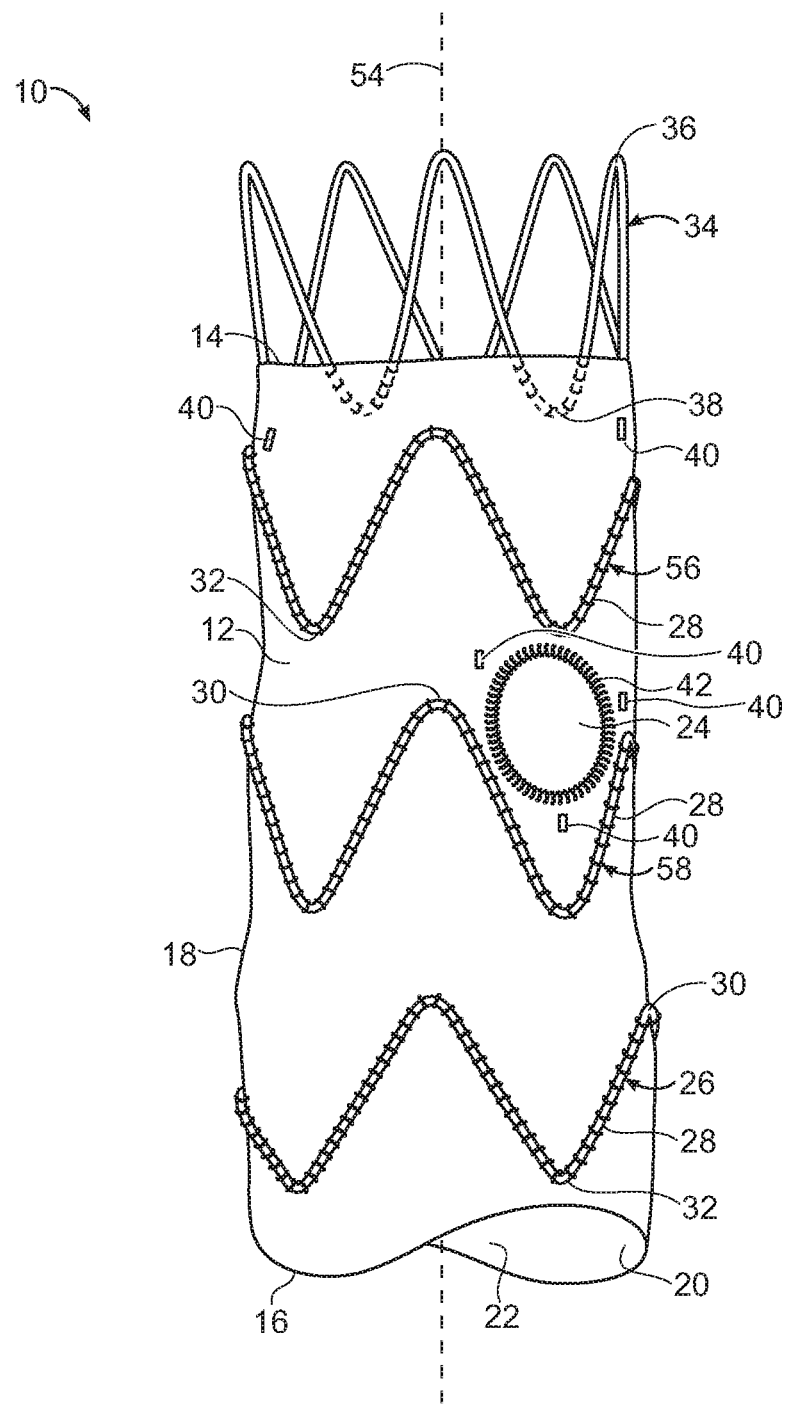
FIG. 1 is a side view of one embodiment of a vascular prosthesis of the invention.

One embodiment of the prosthesis of the invention is shown in FIG. 1. As shown therein, vascular prosthesis 10 includes luminal graft component 12 having proximal open end 14, distal open end 16, outside surface 18, and inside surface 20. Inside surface 20 defines main lumen 22 extending from proximal open end 14 to distal open end 16. Luminal graft component 12 defines fenestration 24 and is formed of a suitable material, such as are known to those skilled in the art, including, for example, at least one member of the group consisting of expanded polytetrafluoroethylene (PTFE), such as ePTFE, and polyethylene terephthalate (PET), such as woven polyester.

Stents 26 extend longitudinally along outside surface 18 of luminal graft component 12, and include struts 28 that join at opposite ends to define proximal apices 30 and distal apices 32. In another embodiment, stents extend longitudinally along inside surface 20 (not shown). In a further embodiment, stents extend longitudinally on inside surface 20 and outside surface 18 (not shown). Bare stent 34 at proximal end 14 includes proximal apices 36 and distal apices 38, and is fixed to inside surface 20 of luminal graft component 12 at distal apices 38. Stents 26,56,58 and bare stent 34 are formed of a suitable material known to those skilled in the art, such as Nitinol or some other suitable shape memory alloy, or stainless steel. Optionally, radiopaque markers 40, such as are known to those skilled in the art, are secured by, for example, suturing or employing a suitable biocompatible adhesive to luminal graft component 12 and about a periphery of fenestration 24. In an embodiment, fenestration ring 42, stents 26 and radiopaque markers 40 includes radiopaque material, such as at least one radiopacifier selected from the group consisting of barium sulfate, bismuth, tungsten, platinum, platinum-iridium, tantalum and tantalum-tungsten.

Fenestration ring 42 encompasses fenestration 24 and is fixed to luminal graft component 12. Fenestration ring 42 is formed of a suitable material, such as Nitinol or some other suitable shape memory alloy, and is fixed to luminal graft component 12 by, for example, sutures, or by using a suitable biocompatible adhesive. In certain embodiments, fenestration ring 42 can be elastic, whereby distortion of fenestration ring 26, by, for example, direction of branch prosthesis as described below, cause radial expansion of the diameter of fenestration 24, fenestration ring 42 exhibits a radially constricting force that can reduce the diameter of fenestration 24 to at least help seal fenestration 24 around the branch prosthesis. In the embodiment shown, fenestration ring 42 borders fenestration 24.

Figure 2A:
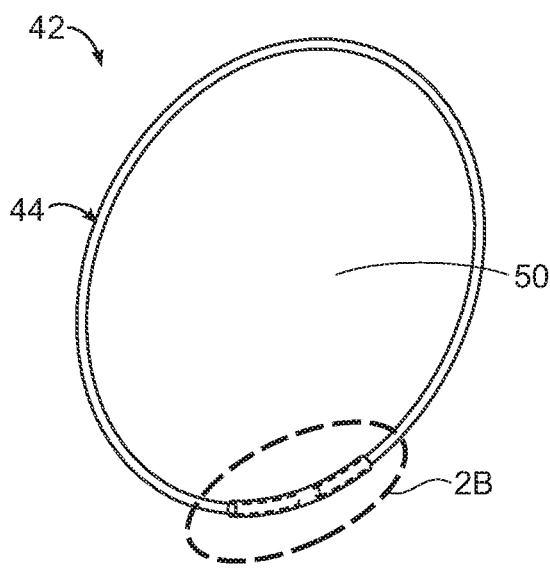
FIG. 2A is a perspective view of one embodiment of a fenestration ring of the vascular prosthesis of the invention shown in FIG. 1.
Figure 2B:
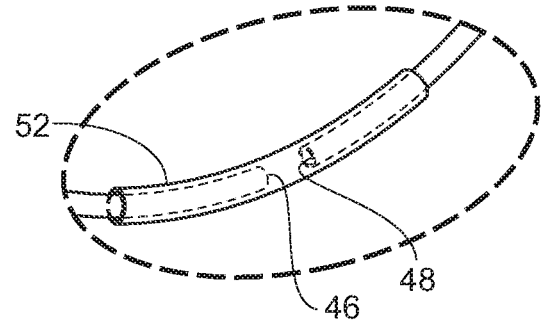
FIG. 2B is a detail of the ends of a main component and a connecting component of the fenestration ring of FIG. 2A.

FIG. 2A is a perspective view of one embodiment of a fenestration ring of a vascular prosthesis of the invention. As shown therein, fenestration ring 42 includes main component 44 and defines opposing ends 46,48 (FIG. 2B). Connecting component 52 of fenestration ring 42 connects opposing ends 46,48. In one embodiment, opposing ends 46,48 oppose each other as a consequence of connection by connecting component 52. FIG. 2B is a detail of FIG. 2A.

Figure 3:
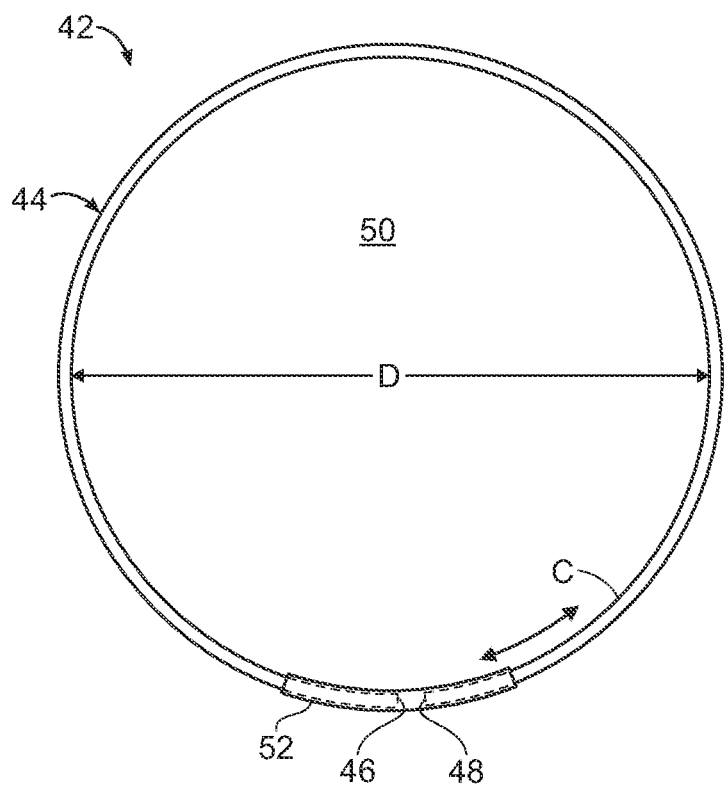
FIG. 3 is a side view of the fenestration ring of FIGS. 2A and 2B.

FIG. 3 is a side view of fenestration ring 42 of FIGS. 2A and 2B. As shown in FIG. 3, fenestration ring 42 defines internal diameter D and internal circumference C. In one embodiment, connecting component 52 is fixed at one end 46 of fenestration ring 42 and slideably engaged to opposite end 48 of fenestration ring 42. Connecting component 52 can be fixed to end 46 of main component 44 by a suitable method, such as by crimping, pinning, or by thermally shrinking connecting component 52 about main component 44. In another embodiment, described below connecting component 52 is slideably engaged with main component 44 at both opposing ends 46,48. In still another embodiment, as more fully described below, connecting component 52 is fixed to both opposing ends 46,48 and varies in length as measured along the perimeter or circumference C of main component 44 between opposing ends 46,48, such as by distending a spring that connects opposing ends 46,48.

As will be explained below, fenestration ring opening 50 and, consequently, variable diameter D of fenestration ring 42 can expand upon insertion of a branch prosthesis through fenestration 24 (FIG. 1) and fenestration ring opening 50 (FIG. 3) during implantation of a branch prosthesis. The manner of fixation of fenestration ring 50 to luminal graft component 12 (FIG. 1) causes expansion of fenestration ring variable diameter D (FIG. 3) from an initial radially contracted diameter to a radially expanded diameter by for example, radial expansion of a branch prosthesis (not shown) that extends through opening 50. Fenestration 24 (FIG. 1) and fenestration ring 42 (FIG. 3) can be circular, oval, round, rectangular, elliptical or some other suitable shape.

Referring back to FIG. 1, in the embodiment of the invention represented therein, proximal apices 30 of stents 26 immediately proximal and distal to fenestration 24 of luminal graft component 12 are substantially longitudinally aligned, parallel to longitudinal axis 54, and distal apices 32 of stents 26 immediately proximal and distal to fenestration 24 of luminal graft are also longitudinally aligned parallel to longitudinal axis 54, whereby a general wave-form created by proximal apices 30 of immediately proximal and immediately distal stents 26 are substantially in-phase.

Figure 4:
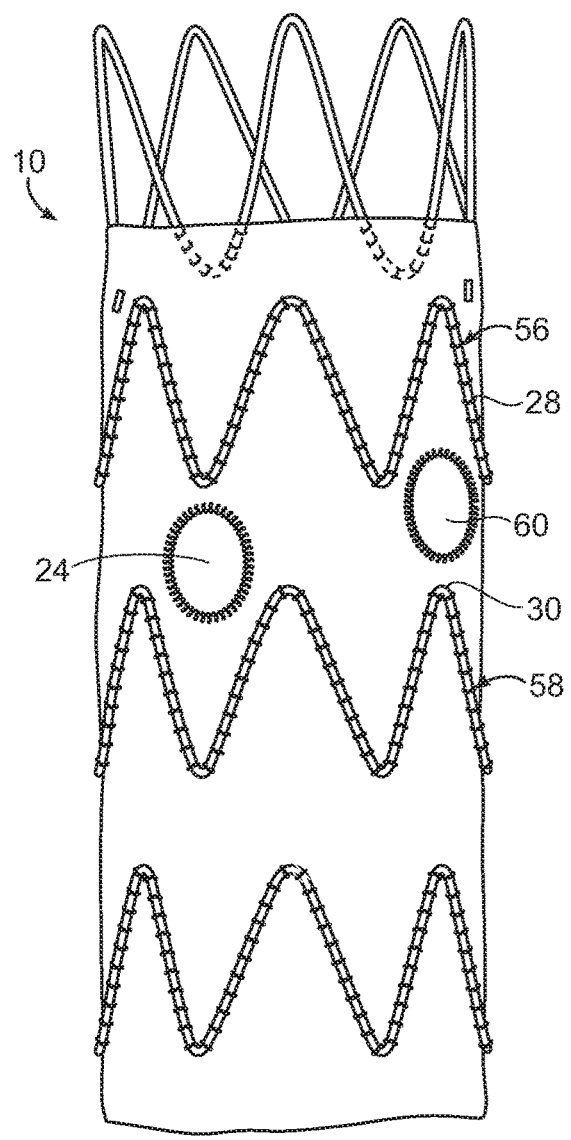
FIG. 4 is a side view of another embodiment of a vascular prosthesis of the invention, including two fenestrations and two corresponding fenestration rings, wherein one fenestration ring is distal to a distal apex of a stent immediately proximal to the fenestration ring and nested between struts of a stent immediately distal to the fenestration ring, and the other fenestration ring is nested between struts of a stent immediately proximal to the fenestration ring and proximal to a proximal apex of a stent immediately distal to the fenestration ring.

In this embodiment, fenestration 24 and fenestration ring 42 lie distal to distal apices 32 of immediately proximal stent 56 and are nested between struts 28 of immediately distal stent 58. It is to be understood that multiple fenestrations and associated fenestration rings can be similarly disposed in alternative embodiments of vascular prosthesis 10. For example, as shown in FIG. 4, an additional or alternative fenestration 60 can be nested between struts 28 of immediately proximal stent 56 and proximal apices 30 of immediately distal stent 58. Likewise, additional or alternative fenestrations can be located in the same or similar arrangements between struts and apices of proximal stent 56 and bare stent 34 (not shown).

Figure 5:
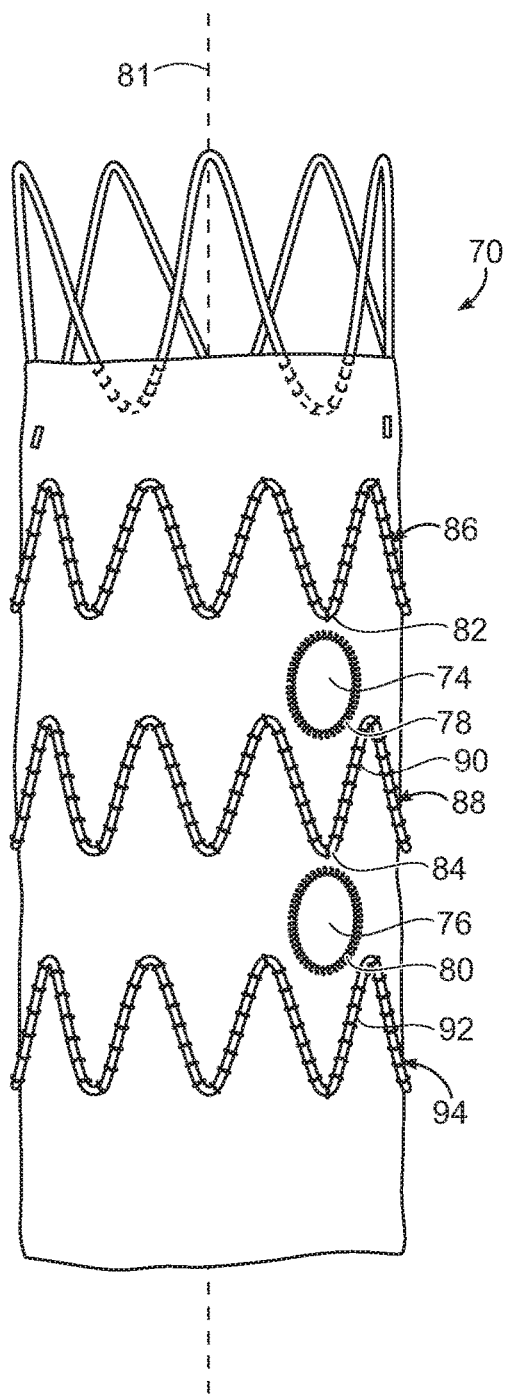
FIG. 5 is a side view of yet another embodiment of a vascular prosthesis of the invention, including two fenestrations and two corresponding fenestration rings, wherein the fenestrations are longitudinally aligned along a longitudinal axis of the vascular prosthesis, and wherein each fenestration and associated fenestration ring is distal to a distal apex of a stent immediately proximal to the fenestration and nested between struts of a stent immediately distal to the fenestration.

In still another embodiment, a plurality of fenestrations and associated fenestration rings can be aligned longitudinally along a vascular prosthesis of the invention. For example, FIG. 5 is an embodiment of the invention wherein vascular prosthesis 70 includes fenestrations 74,76 and associated fenestration rings 78,80, respectively, that are aligned along longitudinal axis 81. In this embodiment, fenestrations 74,76 and associated fenestration rings 78,80, respectively, lie distal to distal apices 82,84 of immediately proximal stent 86,88, and are nested between struts 90,92 of stents 88,94, respectively.

Figure 6:
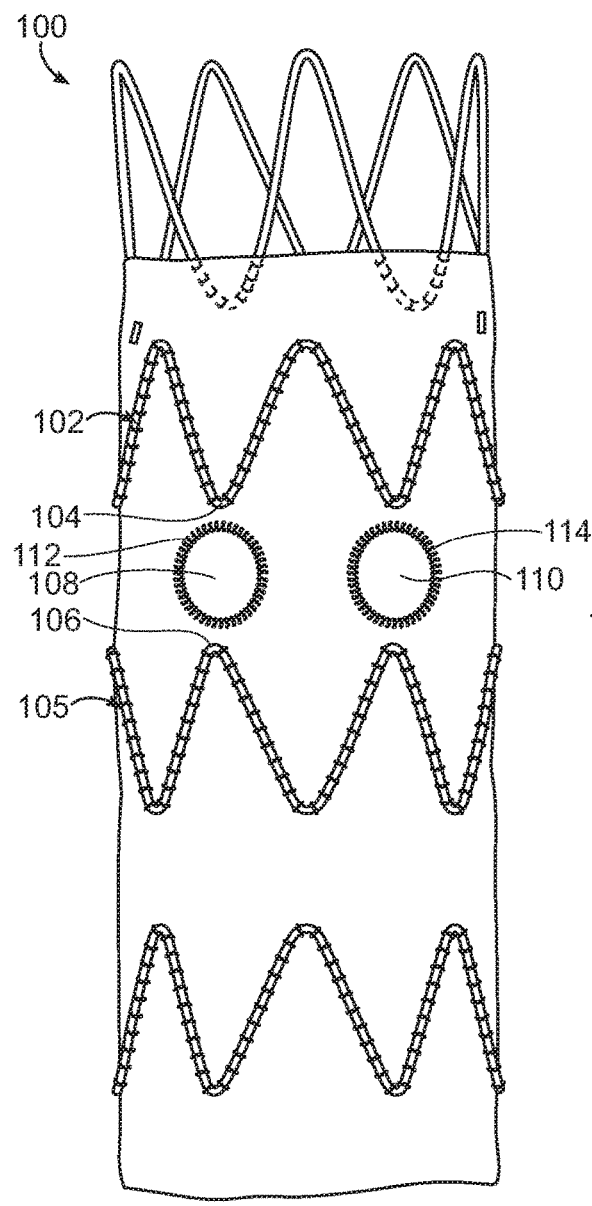
FIG. 6 is a side view of still another embodiment of a vascular prosthesis of the invention, including two fenestrations and two corresponding fenestration rings, wherein fenestrations are positioned laterally relative to each other and are each distal to a distal apex of the immediately proximal stent and proximal to a proximal apex of the immediately distal stent.
Figure 7:
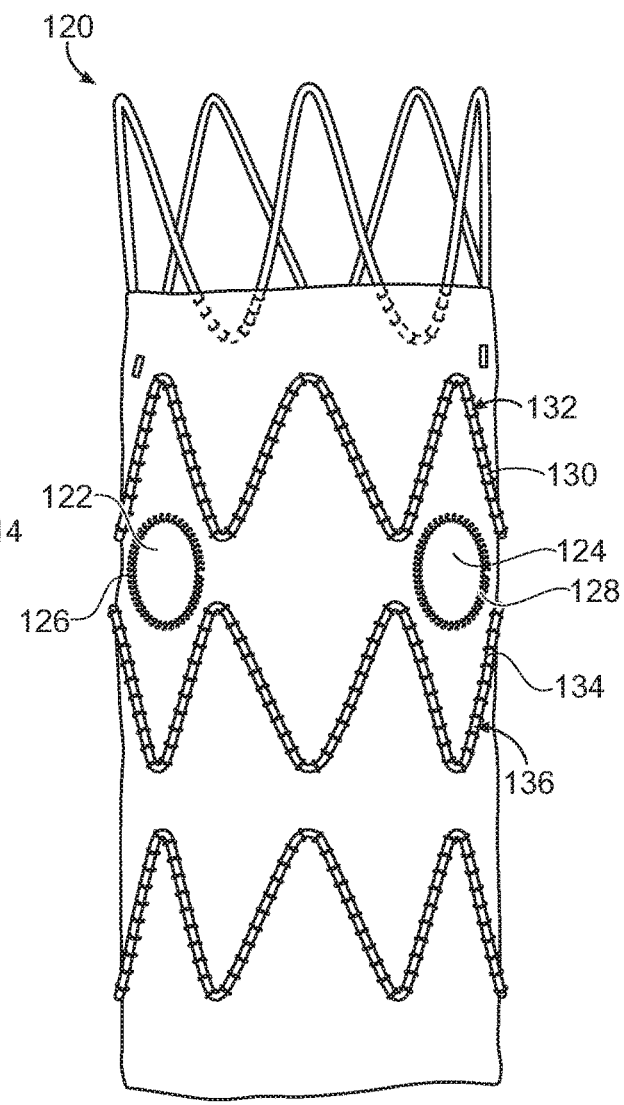
FIG. 7 is a side view of another embodiment of a vascular prosthesis of the invention, including two fenestrations and two corresponding fenestration rings, wherein the fenestrations are positioned laterally relative to each other and are each nested between struts of stents immediately proximal and immediately distal to the fenestration.
Figure 8:
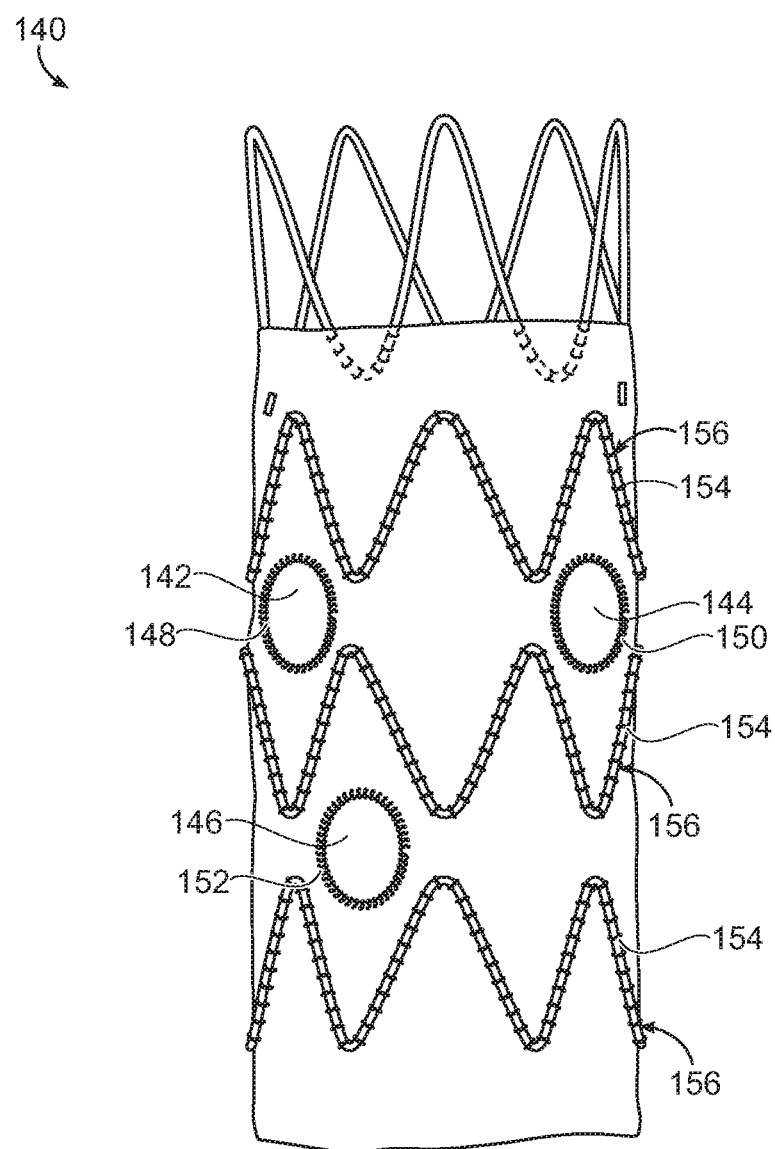
FIG. 8 is a side view of another embodiment of a vascular prosthesis of the invention, including three fenestration and three corresponding fenestration rings, wherein two of the fenestrations are aligned neither laterally nor longitudinally relative each other, and wherein all fenestrations are nested between struts of immediately proximal and immediately distal stents.

FIG. 6 is another example embodiment of a vascular prosthesis of the invention. As shown therein, vascular prosthesis 100 includes stents 102,105. Stent 102 includes distal apices 104 and stent 105 includes proximate apices 106 that are longitudinally aligned. Fenestrations 108,110 and associated fenestration rings 112,114 of the embodiment shown lie between distal apices 104 of immediately proximal stent 102 and immediately proximal to proximal apices 106 of stent 105 immediately distal to fenestrations 108,110, respectively. In yet another embodiment, shown in FIG. 7, vascular prosthesis 120 includes fenestrations 122,124 and associated fenestration rings 126,128, which are arranged laterally and nested between struts 130 of immediately proximal stent 132 and struts 134 of immediately distal stent 136. In still another embodiment, shown in FIG. 8, vascular prosthesis 140 includes fenestrations 142,144,146 and associated fenestration rings 148,150,152, respectively. Fenestrations need not be laterally or longitudinally aligned. For example, fenestration 146 is neither longitudinally aligned nor laterally aligned with either of fenestrations 142,144. Fenestrations 142,144,146 of the embodiment of FIG. 8 lie nested between struts 154 of immediately proximal and distal stents 156. It is to be understood that different combinations of the arrangements identified in FIGS. 1, and 4 through 8, are also various embodiments of the vascular prosthesis of the invention. It is also to be understood that, in certain embodiments of the invention, fenestrations and associated rings of embodiments can be arranged independently of the position of any stent component of the vascular prosthesis of the invention.

Figure 9:
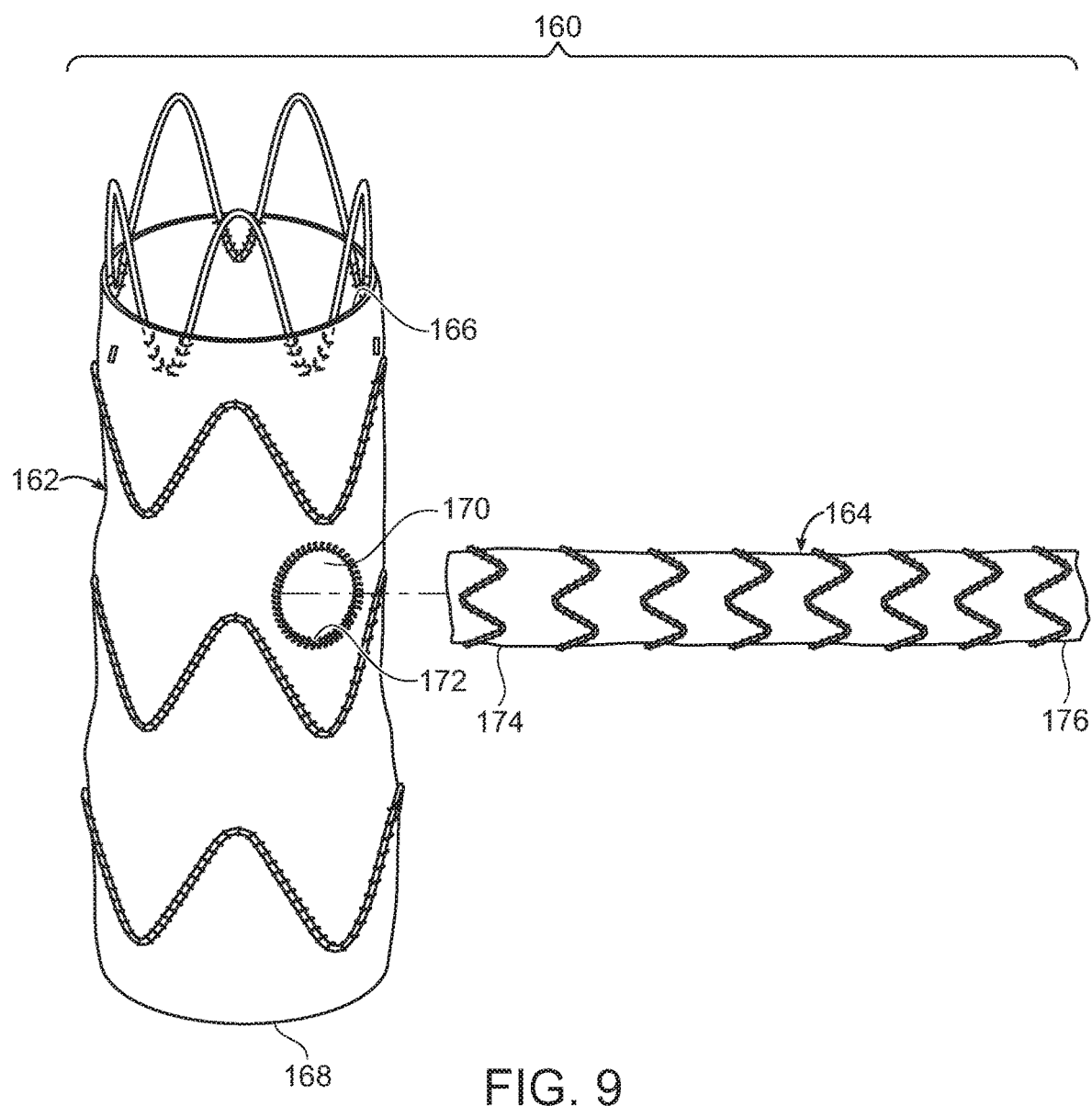
FIG. 9 is an exploded view of a combination of a vascular prosthesis of the invention and a branch prosthesis suitable for use with the vascular prosthesis of the invention.
Figure 10:
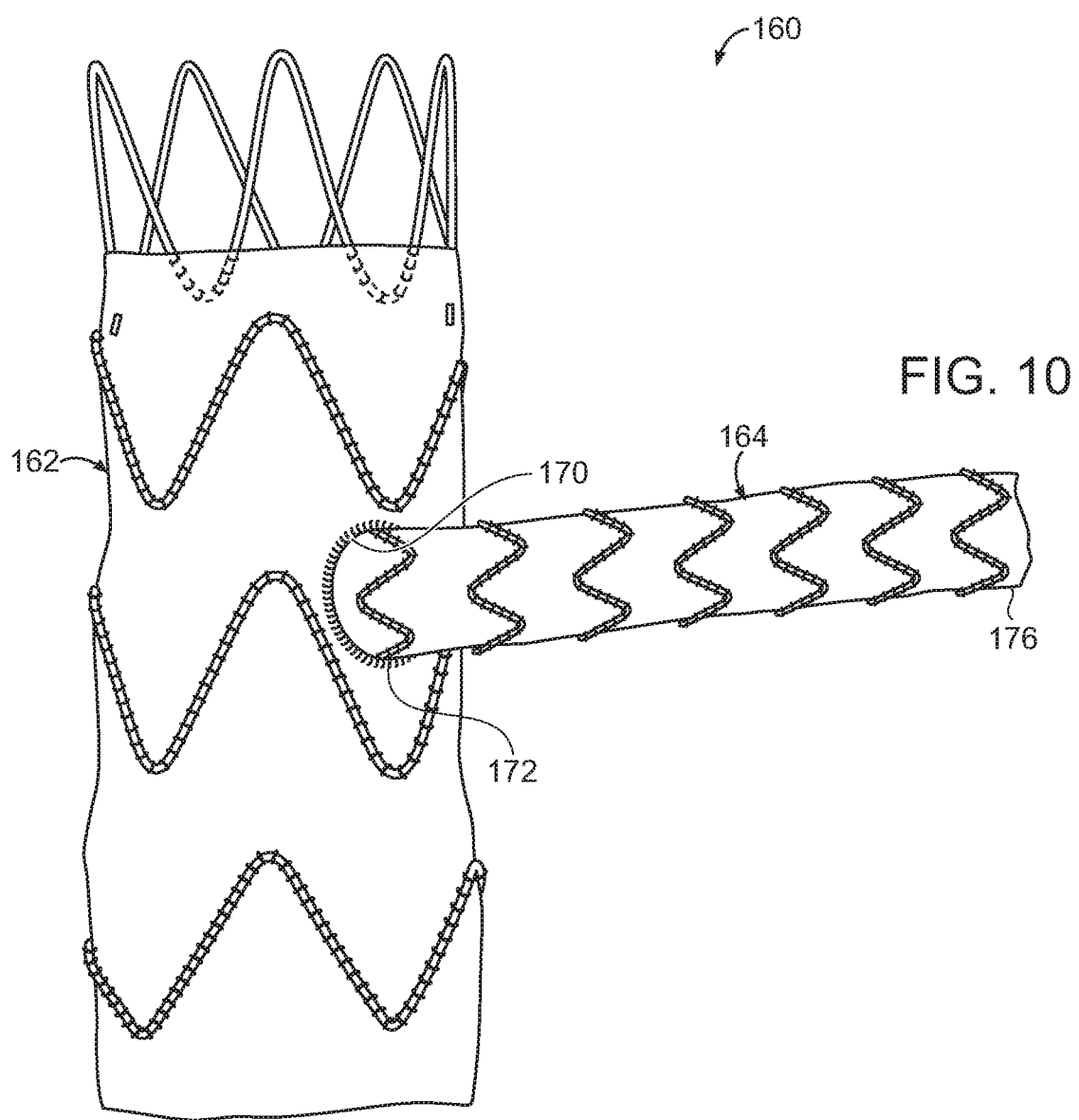
FIG. 10 is an assembled view of the combination shown in FIG. 9.

FIG. 9 is an exploded view of an embodiment of a vascular prosthesis assembly 160 of the invention. As shown therein, vascular prosthesis assembly 160 includes vascular prosthesis main body 162 and least one branch prosthesis 164. Vascular prosthesis main body 162 includes proximal end 166 and distal end 168, and defines fenestration 170 that is encompassed by fenestration ring 172. Branch prosthesis 164 includes proximal end 174 and distal end 176. When assembled, branch prosthesis 164 extends through fenestration 170 and expanded fenestration ring 172, as shown in FIG. 10.

Figure 11:
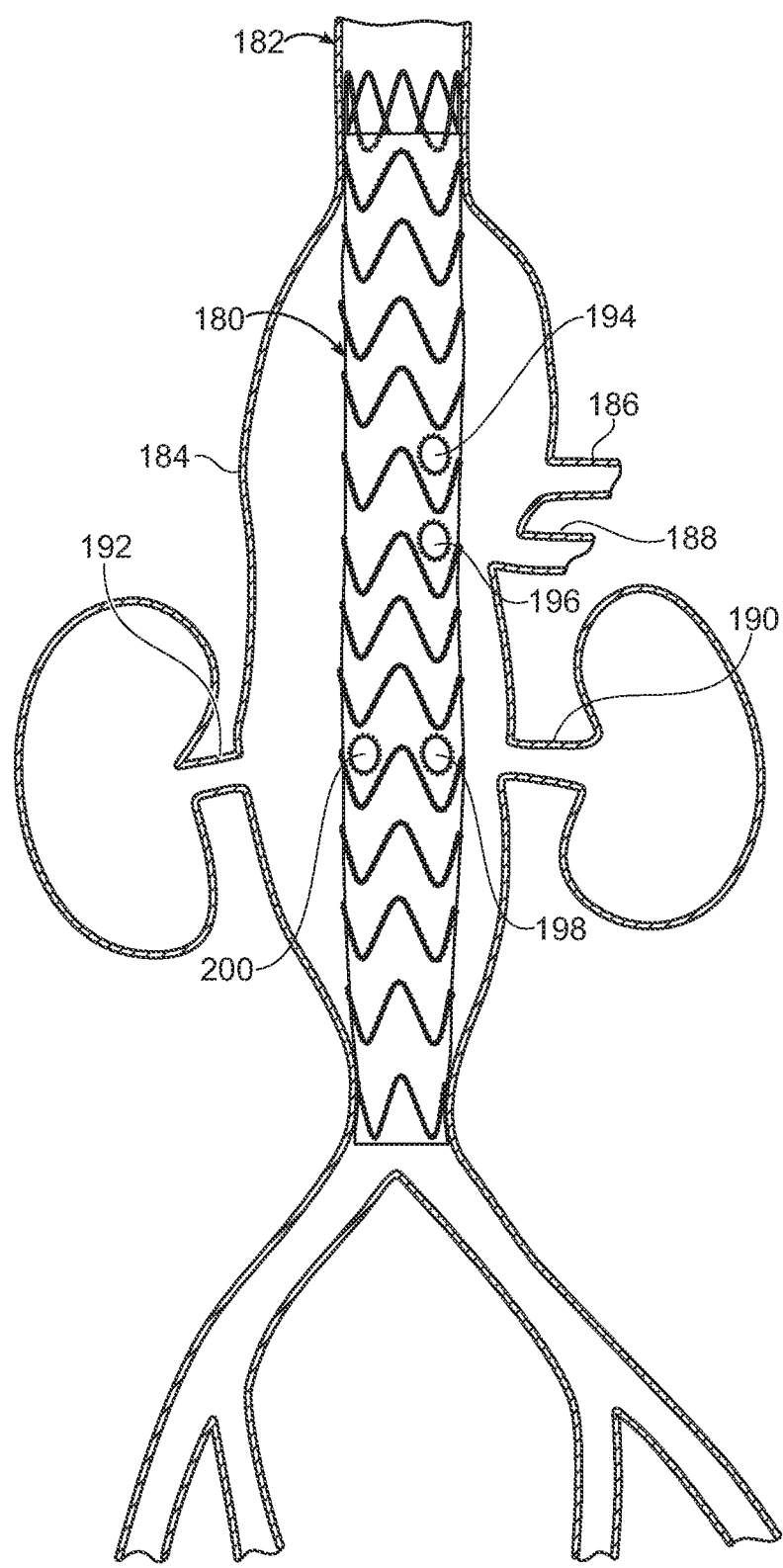
FIG. 11 is a side view of an embodiment of a vascular prosthesis of the invention implanted at an aneurysm site.
Figure 12:
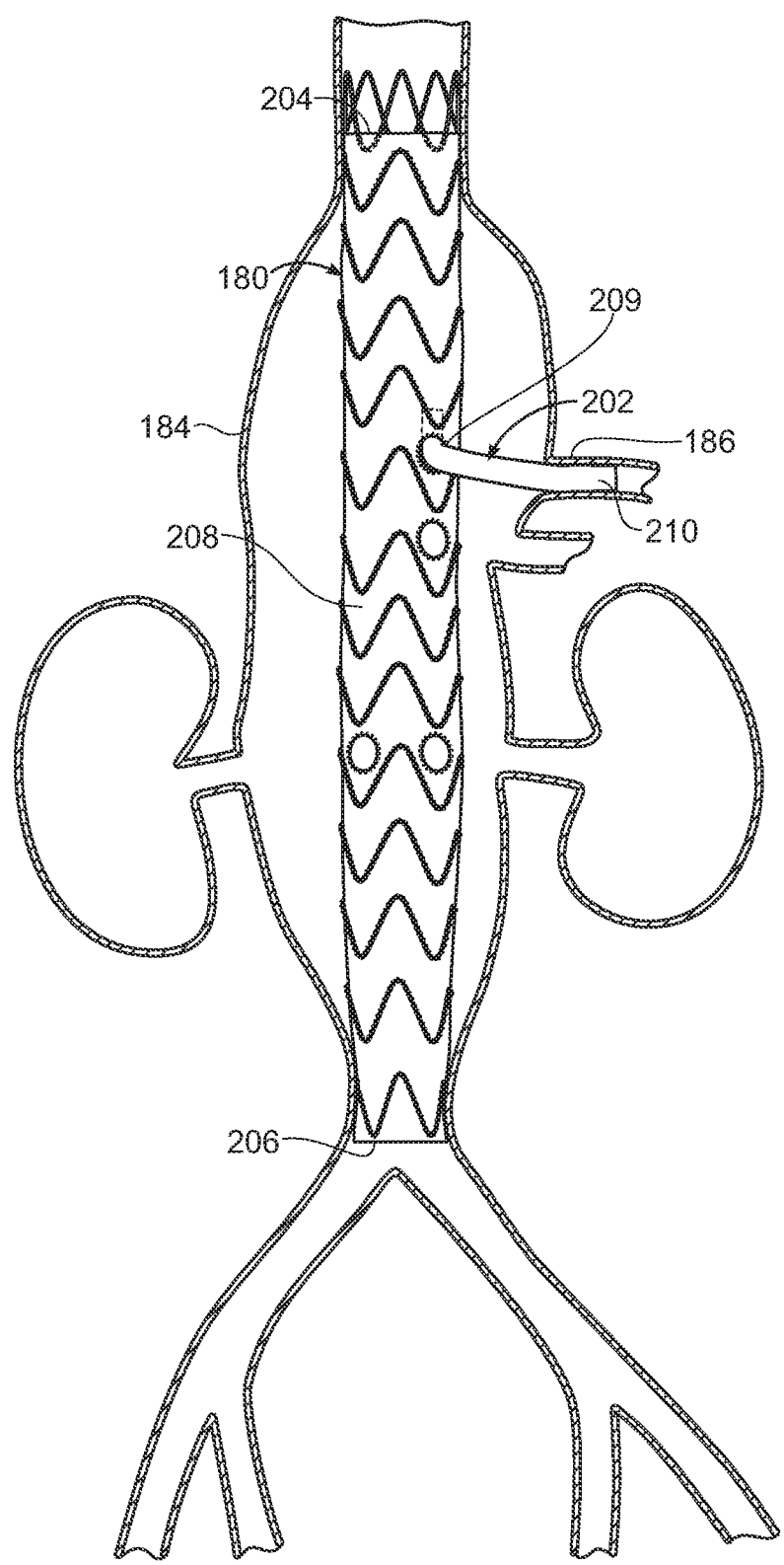
FIG. 12 is a side view of the vascular prosthesis shown in FIG. 11, with one branch prosthesis having been implanted through a fenestration and fenestration ring of the vascular prosthesis shown in FIG. 11.

In another embodiment, the invention is a method for treating an aortic aneurysm. For example, with reference to FIG. 11, vascular prosthesis 180 is delivered through aorta 182 to aneurysm site 184 of a patient, such as by radially and releasably constricting vascular prosthesis 180 by a vascular prosthesis delivery device, not shown. In this embodiment shown in FIG. 11, aneurysm 184 spans a region of the aorta that includes the celiac artery 186, the superior mesenteric artery 188, and left and right renal arteries 190,192, respectively. Vascular prosthesis includes four fenestration, 194, 196,198,200, each of which includes an associated fenestration ring which is aligned with a corresponding arterial branch of the aorta at the aneurysm site of the patient. Vascular prosthesis 180 is then released from the vascular delivery device and the delivery device is removed from the patient. As shown in FIG. 12, branch prosthesis 202 is delivered by the branch prosthesis delivery device (not shown) through proximal open end 204 or distal open end of luminal graft component 208 of the vascular prosthesis 180. Branch prosthesis 202 is then directed through fenestration 194 and the associated fenestration ring 209, and distal end 210 of branch prosthesis 202 is implanted in celiac artery 186. Proximal end 209 of branch prosthesis 202 is fixed at fenestration 194 of vascular prosthesis 180.

The vascular prostheses of the invention, and the branch prosthesis included in vascular prosthesis assemblies of the invention can be implanted by, for example, a delivery device, such as is known in the art. One embodiment of a delivery device known in the art is shown in FIGS. 13 and 14A through 14C.

FIG. 13 is an exploded side view of a prior art delivery device suitable for delivering a vascular prosthesis of the invention. As can be seen in FIG. 13, delivery device 230 includes guidewire catheter 232 having proximal end 234 and distal end 236. Proximal handle 238 is fixed to proximal end 234 and nose cone 240 is fixed to distal end 236. Introducer sheath 242 has proximal end 244 and distal end 246. Distal handle 248 is fixed to proximal end 244. Introducer sheath 242 can be rigid or flexible.

FIG. 14A is a side view of the delivery device 230 when assembled. As can be seen therein, introducer sheath 242 and distal handle 248 extend around guidewire catheter 232. Although not shown, a vascular prosthesis of the invention is held in a radially constrained position around guidewire catheter 232 and within introducer sheath 242. In a method of the invention, the vascular prosthesis is implanted at aneurysm 243 by advancing delivery device 230 within an artery of a patient until the vascular prosthesis is at aneurysm site 243. Distal handle 248 is then retracted along guidewire catheter 232 and toward proximal handle 238, as shown in FIG. 14B, thereby retracting introducer sheath 242 from around vascular prosthesis 250 defining fenestration 181, as indicated by arrow 241. Vascular prosthesis 250 is released from its radially constricted position and radially expands to a radially expanded position, such as by use of a balloon catheter, or by use of radially self-expanding stents, as is known in the art, and is thereby deployed at aneurysm 243. In an embodiment, vascular prostheses 242 includes burp stent 245. Delivery device 230 thereafter is removed from the patient, as shown in FIG. 14C. The same or a similar delivery device can be employed to deliver or implant one or more branch prostheses 257 through a respective fenestrations of a vascular prosthesis of the invention and into arterial branch 259, thereby completing implantation of vascular prosthesis 250 and treatment of aneurysm 243. It is to be understood that, alternatively, other suitable types of aortic prosthesis delivery devices, such as are known in the art, can be employed.

Figure 15:
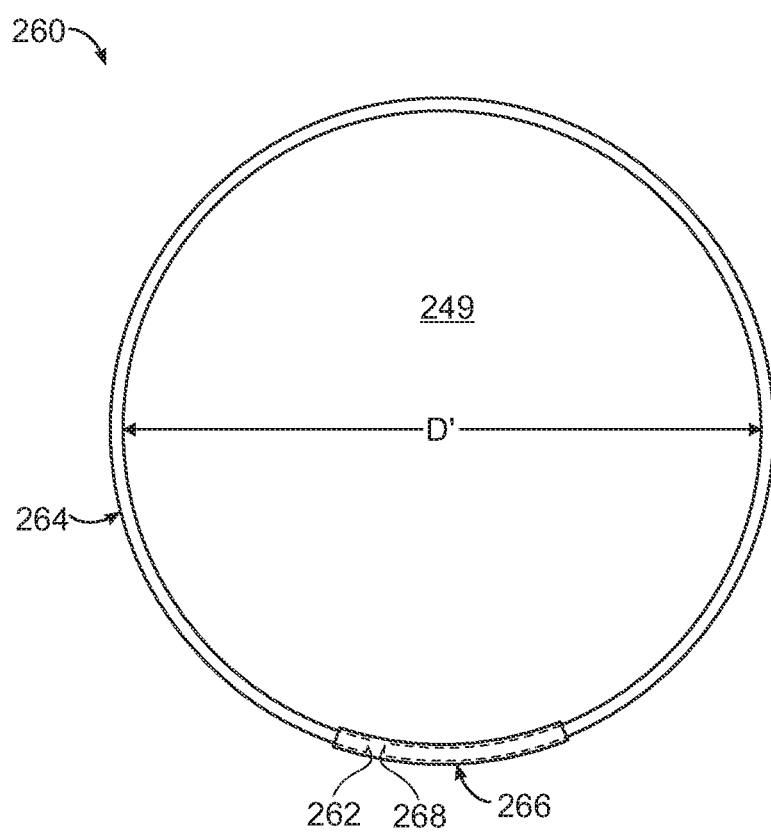
FIG. 15 is a side view of a fenestration ring of a vascular prosthesis of the invention wherein one end of the main component of the fenestration ring is fixed to a connecting component of the fenestration ring, and wherein fenestration ring has a radially contracted diameter D'.
Figure 16:
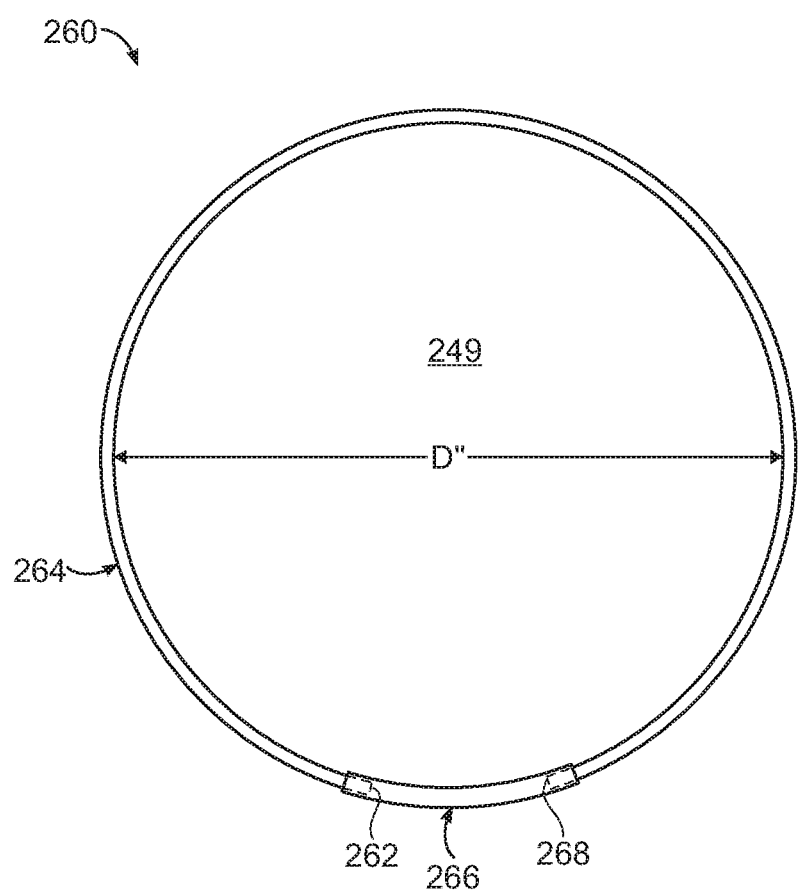
FIG. 16 is a side view of the fenestration ring of FIG. 15, wherein the fenestration ring has a radially expanded diameter D".
Figure 17:
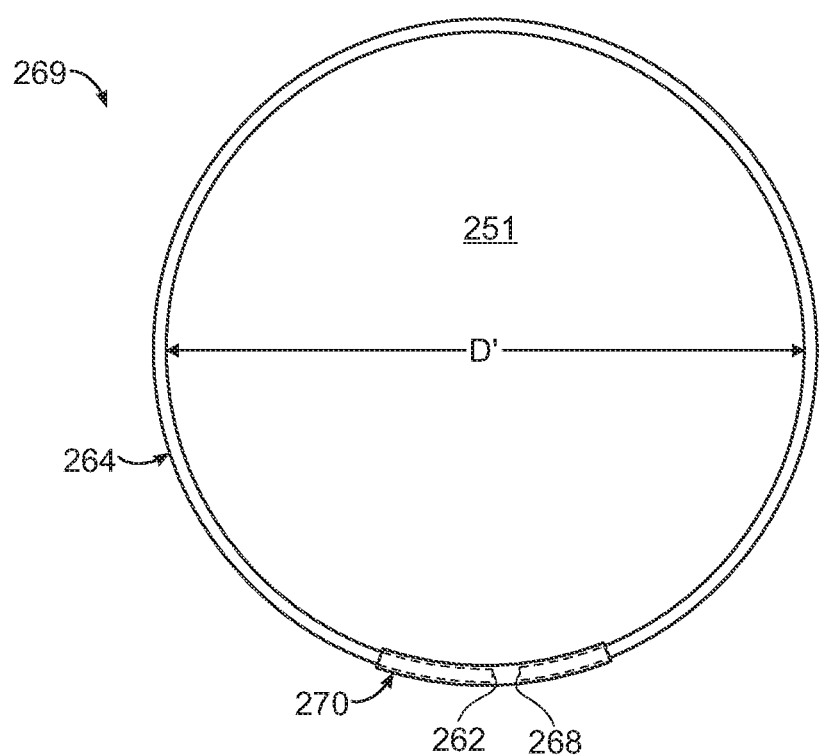
FIG. 17 is a side view of a fenestration ring of another embodiment of a vascular prosthesis of the invention, wherein both ends of main component of the fenestration ring are slideably engaged with a connecting component of the fenestration ring and wherein the fenestration ring has a contracted diameter D'.
Figure 18:
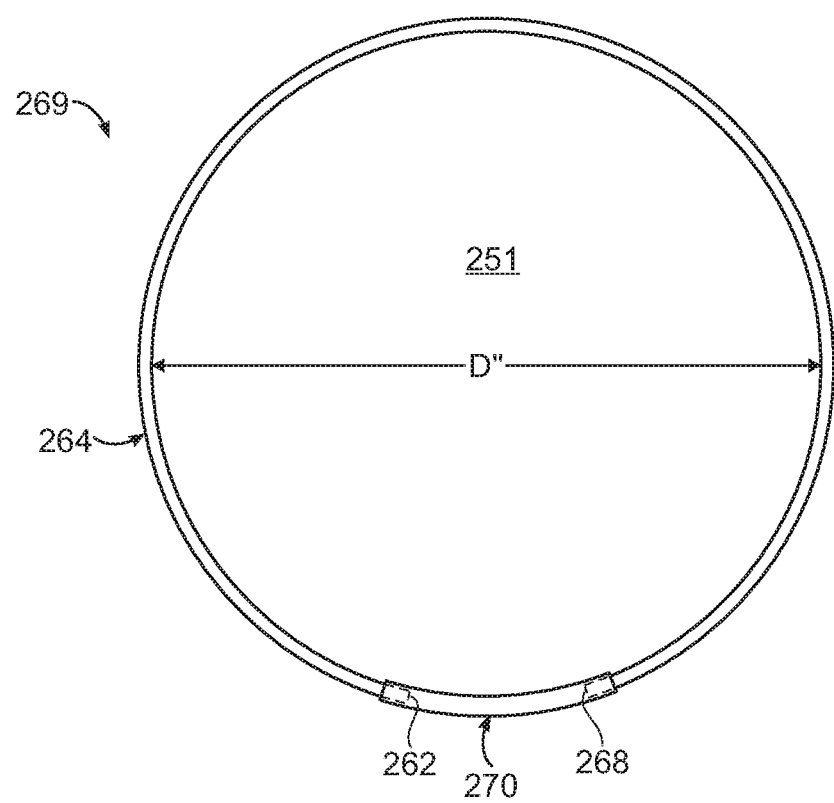
FIG. 18 is a side view of the fenestration ring of FIG. 17, where this fenestration ring has an expanded diameter D".
Figure 19:
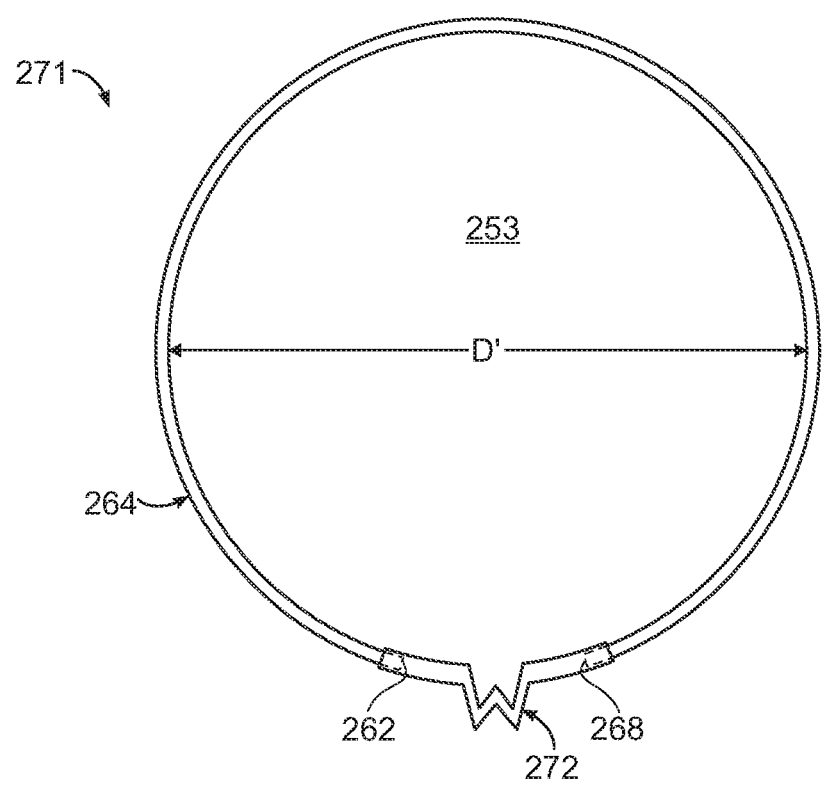
FIG. 19 is a side view of a fenestration ring of another embodiment of the invention, wherein the connecting component is fixed to both ends of the main component and is a spring, and wherein the fenestration ring has a diameter D'.
Figure 20:
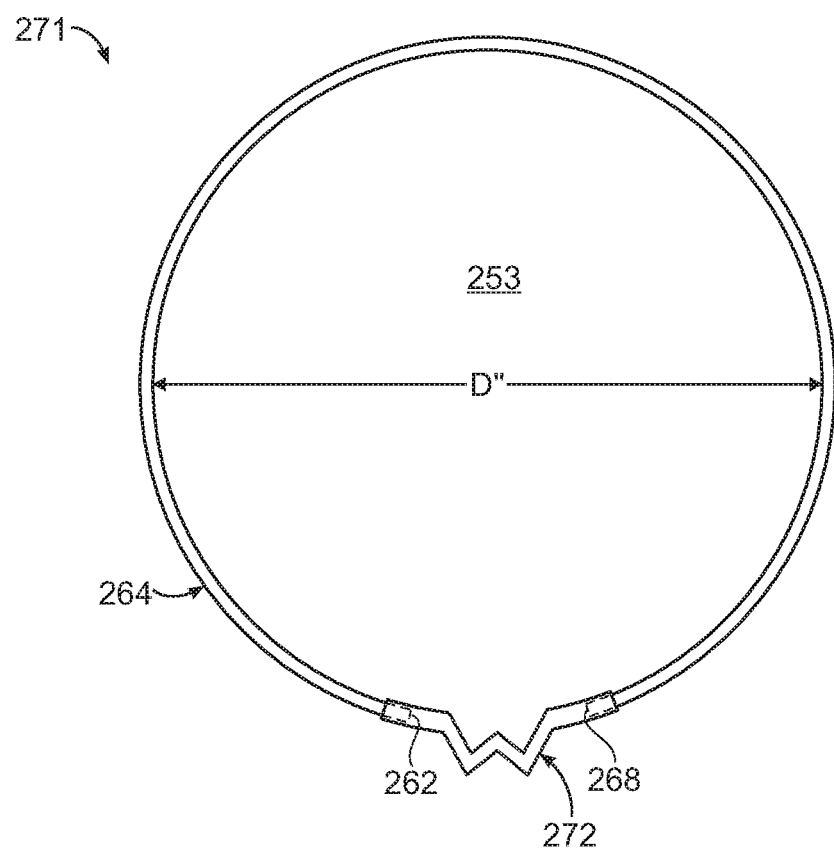
FIG. 20 is a side view of the fenestration ring of FIG. 19, wherein the fenestration ring has an expanded diameter D".

During delivery of branch prosthesis through a fenestration and associated fenestration ring by a method of the invention, fenestration ring 260, for example, shown in FIGS. 15 and 16, expands in diameter D from a first, contracted diameter D', shown in FIG. 15, to a second, expanded diameter D", shown in FIG. 16. As shown in the transition from FIG. 15 to FIG. 16, end 262 of ring main component 264 is fixed to connecting component 266, while end 268 of main component 264 is slideably engaged with connecting component 266, whereby expansion of diameter D from D' to D" causes end 268 to partially withdraw from connecting component 266, thereby increasing the area of fenestration ring opening 249. Alternatively, as shown in FIGS. 17 and 18, fenestration ring 269 includes main component 264 having ends of diameter D 262,268 that are both slideably engaged with connecting component 270, whereby expansion from D' to D" by direction of the branch prosthesis through the fenestration and fenestration ring opening 251 causes both ends 262,268 to partially withdraw from connecting component 266. In still another embodiment, shown in FIGS. 19 and 20, connecting component 272 is fixed to both ends 262,268 of main component 264. Connecting component 272 of fenestration ring 271 is a spring, formed of a suitable material, such as Nitinol or some other shape memory alloy, or stainless steel, and extends in length between ends 262,268 as main component 264 increases in diameter from contracted diameter D' to expanded diameter D". Connecting component 272 can exhibit elastic or shape memory properties, whereby, following implantation of a branch prosthesis through opening 253, ends 262,268 are drawn closer together, thereby reducing the radial diameter D of opening 253 from D" to a smaller radial diameter D.

In any of these embodiments, main component 264, by expanding in diameter enough to allow passage of branch prosthesis through the fenestration and radially expand against and thereby abut main component 260, at least assists in creating a seal at the juncture between the fenestration and the branch prosthesis. In some embodiments, fenestration ring is elastic, or exhibits shape memory, whereby, following implantation of a branch prosthesis, fenestration ring constricts to a diameter less than that of D" to create a mechanical lock. Further, the position of fenestration ring relative to stents of the vascular prosthesis immediately proximal and distal to the fenestration ring 20 can also facilitate formation of a seal at the juncture between each fenestration and a corresponding branch prosthesis.

Figure 21:
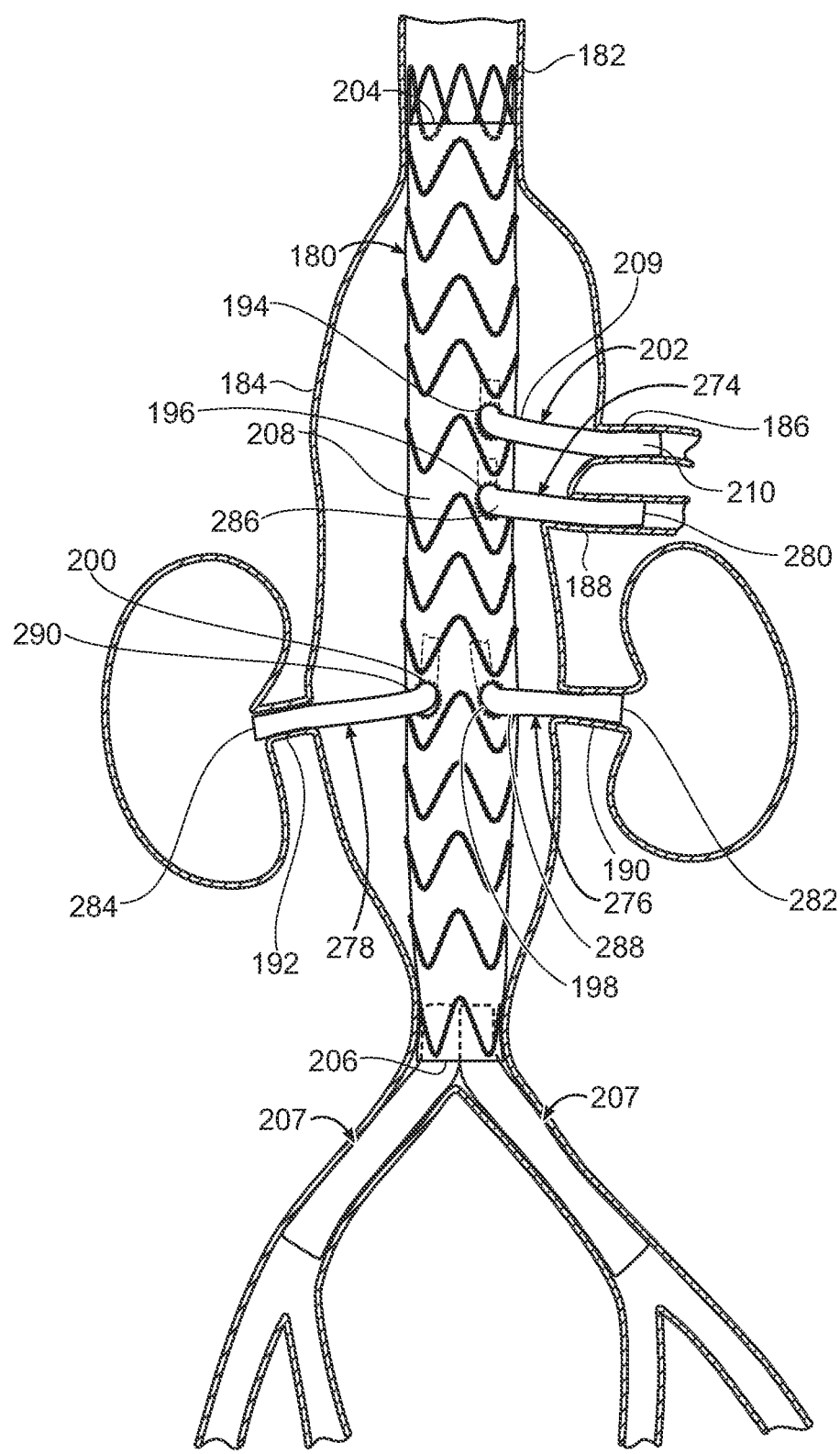
FIG. 21 is a side view of the vascular prosthesis of FIGS. 11 and 12, wherein branch prostheses have been implanted through respective fenestrations and associated fenestration rings of the vascular prosthesis of the invention.

As can be seen in FIG. 21, and further to the embodiment shown in FIG. 12, branch prostheses 274,276,278 are delivered through each corresponding fenestration 196,198,200 and extend from each corresponding fenestration. Distal ends 280,282,284 are each directed by a respective branch prosthesis delivery device (not shown) into a respective branch 188,190,192 of aorta 182 at aneurysm 184, and secured by a fenestration ring in respective fenestrations 196,198,200 at proximal ends 286,288,290 and within branch artery 188,190,192 at distal ends 278,280,282. Proximal ends 286,288 and 290 of respective branch prostheses 274,276,278 are fixed at respective fenestrations 196,198, 200. Each branch prosthesis 274,276,278 is then released from the respective branch prosthesis delivery device. The vascular prosthesis delivery device and the branch prosthesis delivery device are then removed either simultaneously or, in sequence, thereby completing implantation and treatment of the aneurysm. In an embodiment, additional branch prostheses 207 can be implanted into distal end 206 of vascular repair device 180.

Although not shown, the distal end of the vascular repair device of the invention can be bifurcated and additional prostheses can be implanted into the distal end of the bifurcated vascular prosthesis.

Vascular prostheses of the invention can be implanted, for example, by transfemoral access. Additional branch prostheses that are directed into the vascular prostheses of the invention can be implanted, for example, by supraaortic vessel access (e.g., through the brachial artery), or by transfemoral access, or access from some other branch or branch of major blood vessels, including peripheral blood vessels.

The teachings of all patents, published applications and references cited herein are incorporated by reference in their entirety. The relevant teachings of U.S. Pat. Nos. 8,292,943; 7,763,063; 8,308,790; 8,070,790; 8,740,963; 8,007,605; 9,320,631; 8,062,349; 9,198,786; 8,062,345; 9,561,124; 9,173,755; 8,449,595; 8,636,788; 9,333,104; 9,408,734; 9,408,735; 8,500,792; 9,220,617; 9,364,314; 9,101,506; 8,998,970; 9,554,929; 9,439,751; 9,592,112; 9,655,712; 9,827,123, 9,877,857, 9,907,686; U.S. patent application Ser. Nos. 14/575,673; 15/166,818; 15/167,055; 14/272,818; 14/861,479; 15/478,424; 15/478,737; 15/587,664; 15/604, 032; 15/672,404; 15/816,772; 15/839,272; 15/417,467; PCT/US2017/025844; PCT/US2017/025849; PCT/US2017/ 025912; PCT/US2017/034223 and PCT/US2017/046062, are also incorporated by reference in their entirety.

The relevant teachings of Published Patent Cooperation Treaty (PCT) Application Nos.: PCT/US2018/019355; PCT/ US2018/019344; PCT/US2018/019349; PCT/US2018/ 019353; PCT/US2018/019354; PCT/US2018/019352; PCT/ US2018/019342; PCT/US2018/019350; PCT/US2018/ 019356; and PCT/US2018/019510, are also incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A vascular prosthesis, comprising:
 a) a luminal graft component having a proximal open end, a distal open end, and defines a main lumen extending from the proximal open end to the distal open end, the luminal graft component defining at least one fenestration having a circumference; and
 b) at least one fenestration ring encompassing the at least one fenestration and fixed to the luminal graft component, the at least one fenestration ring defining a variable fenestration ring diameter and including a main component having two non-overlapping opposing ends in a radially contracted configuration, and a connecting component that bridges and covers the two non-overlapping opposing ends the connecting component enclosing each end of the main component to thereby complete configuration of the main component as a ring, wherein the fenestration ring diameter can expand upon insertion of a branch prosthesis through the at least one fenestration ring during implantation of the branch prosthesis.

2. The vascular prosthesis of claim 1, further including at least one radially-expanding stent at the luminal graft component.

3. The vascular prosthesis of claim 2, wherein a plurality of stents are arranged along at least a portion of a length of the luminal graft component.

4. The vascular prosthesis of claim 3, wherein the fenestration ring is between two of the stents.

5. The vascular prosthesis of claim 4, wherein at least one of the stents immediately proximal to the ring and immediately distal to the ring include struts that are joined to define proximal apices and distal apices of the stent.

6. The vascular prosthesis of claim 5, wherein both the stent immediately proximal to and the stent immediately distal to the ring include struts that each define distal and proximal apices.

7. The vascular prosthesis of claim 6, wherein the proximal apices and the distal apices are each longitudinally aligned along the luminal graft component.

8. The vascular prosthesis of claim 7, wherein the ring is distal to a distal apex of the immediately proximal stent and nested between struts of the immediately distal stent.

9. The vascular prosthesis of claim 7, wherein the ring is proximal to a proximal apex of the immediately distal stent and nested between struts of the immediately proximal stent.

10. The vascular prosthesis of claim 6, wherein the immediately proximal and immediately distal stents include proximal and distal apices that are 180° out of phase.

11. The vascular prosthesis of claim 10, wherein the ring is longitudinally between the proximal apex of the immediately distal stent and the distal apex of the immediately proximal stent.

12. The vascular prosthesis of claim 11, wherein the ring is nested between stents of the immediately proximal and immediately distal stents.

13. The vascular prosthesis of claim 1, wherein the main component includes at least one of a wire and a polymer.

14. The vascular prosthesis of claim 13, wherein the wire includes a shape-memory alloy.

15. The vascular prosthesis of claim 14, wherein the shape memory alloy includes Nitinol.

16. The vascular prosthesis of claim 1, wherein the at least one fenestration ring is sutured to the luminal graft component at the circumference of the fenestration.

17. The vascular prosthesis of claim 1, wherein the vascular prosthesis includes one fenestration and one fenestration ring.

18. The vascular prosthesis of claim 1, wherein the vascular prosthesis includes two fenestrations and two fenestrations rings.

19. The vascular prosthesis of claim 1, wherein the vascular prosthesis includes three fenestrations and three fenestrations rings.

20. The vascular prosthesis of claim 1, wherein the vascular prosthesis includes four fenestrations and four fenestrations rings.

21. The vascular prosthesis of claim 1, further including at least one branch prosthesis, each branch prosthesis having a proximal end and a distal end, and extendable through at least one of the fenestrations.

22. The vascular prosthesis of claim 1, wherein the connecting component is slideably engaged with both ends of the main components.

23. The vascular prosthesis of claim 1, wherein the connecting component is slideably engaged with one of the main component and fixed to the other end of the main component.

24. The vascular prosthesis of claim 1, wherein the connecting component is expandable and is fixed to both ends of the main components.

25. A method for treating an aortic aneurysm, comprising the steps of:
   a) delivering a vascular prosthesis through an artery to an aneurysm of a patient, the aneurysm spanning a region of the artery that includes at least one arterial branch, the vascular prosthesis being radially and radially constricted by a vascular prosthesis delivery device, the vascular prosthesis including:
      i) a luminal graft component having a proximal open end, a distal open end, and defining a main lumen extending from the proximal open end to the distal open end, the luminal graft component defining at least one fenestration having a circumference; and
      ii) at least one fenestration ring encompassing the at least one fenestration and fixed to the luminal graft component, the at least one fenestration ring defining a variable fenestration ring diameter and including a main component having two non-overlapping opposing ends in a radially contracted configuration, and a connecting component that bridges and covers the two non-overlapping opposing ends the connecting component enclosing each end of the main component to thereby complete configuration of the main component as a ring, wherein the fenestration ring diameter can expand upon insertion of a branch prosthesis through the at least one fenestration ring during implantation of the branch prosthesis;
   b) aligning the at least one fenestration with the at least one arterial branch at the aneurysm site of the patient;
   c) delivering at least one branch prosthesis through the proximal open end or the distal open end of the luminal graft component of the vascular prosthesis, and through the fenestration to the arterial branch, the branch prosthesis being radially and releasably constricted by a branch prosthesis delivery device; and
   d) releasing the branch prosthesis from the branch prosthesis delivery device, expansion of the branch prosthesis causing contact at the luminal graft component that increases the variable fenestration ring diameter, thereby forming a seal between vascular prosthesis and the branch prosthesis and treating the aortic aneurysm.

* * * * *